United States Patent
Vandyke

(10) Patent No.: US 12,097,310 B2
(45) Date of Patent: Sep. 24, 2024

(54) APPARATUS AND METHOD FOR IRRADIATING AIR IN AN AIR CIRCULATION SYSTEM OF A VEHICLE

(71) Applicant: THE BOEING COMPANY, Chicago, IL (US)

(72) Inventor: Bryce Vandyke, Everett, WA (US)

(73) Assignee: The Boeing Company, Arlington, VA (US)

(*) Notice: Subject to any disclaimer, the term of this patent is extended or adjusted under 35 U.S.C. 154(b) by 540 days.

(21) Appl. No.: 17/192,395

(22) Filed: Mar. 4, 2021

(65) Prior Publication Data

US 2021/0393841 A1    Dec. 23, 2021

Related U.S. Application Data

(60) Provisional application No. 63/041,717, filed on Jun. 19, 2020.

(51) Int. Cl.
*A61L 9/20* (2006.01)
*A61L 9/014* (2006.01)

(52) U.S. Cl.
CPC ............ *A61L 9/20* (2013.01); *A61L 9/014* (2013.01); *A61L 2209/12* (2013.01);
(Continued)

(58) Field of Classification Search
CPC ........ A61L 9/20; A61L 9/014; A61L 2209/12; A61L 2209/14; A61L 2209/16;
(Continued)

(56) References Cited

U.S. PATENT DOCUMENTS 5,399,319 A * 3/1995 Schoenberger .... B01D 46/0028
                                                    55/385.2
5,997,619 A * 12/1999 Knuth ................ B01D 46/0038
                                                    55/385.2
(Continued)

FOREIGN PATENT DOCUMENTS

CN    103446879 A    12/2013
JP    H10249128 A    9/1998
(Continued)

OTHER PUBLICATIONS

European Extended Search Report and Written Opinion issued in connection with European Application No. 21170882.1 dated Oct. 4, 2021, pp. 12.

(Continued)

*Primary Examiner* — Sean E Conley
*Assistant Examiner* — Brendan A Hensel
(74) *Attorney, Agent, or Firm* — Alleman Hall & Tuttle LLP

(57) ABSTRACT

An apparatus for irradiating air flow in a vehicle includes a filter unit configured to couple to a recirculating-air conduit connected to a manifold of an air circulation system, the filter unit having an inlet end, and a filter disposed in the inlet end of the filter unit, including an outer High Efficiency Particulate Air (HEPA) media. The apparatus further includes a plurality of ultraviolet light transmissive strands that each have distal ends disposed in a spaced apart manner in an interface region between the outer HEPA media filter and an inner activated carbon filter or HEPA filter, and proximal ends connectable to an ultraviolet light emitting source such that ultraviolet light is transmitted by the transmissive strands into the interface region. The transmissive strands are configured to receive emitted ultraviolet
(Continued)

light that is substantially between 222 nm and 265 nm for irradiating air passing through the filter.

20 Claims, 6 Drawing Sheets

(52) U.S. Cl.
CPC ....... *A61L 2209/14* (2013.01); *A61L 2209/16* (2013.01); *A61L 2209/22* (2013.01)

(58) Field of Classification Search
CPC . A61L 2209/22; B60H 3/0078; B60H 3/0658; B60H 2003/0666; B60H 2003/0691; B60H 3/0608; F24F 8/22; F24F 8/10; B64D 13/06; B64D 2013/0688; B64D 13/00; B64D 2013/0603; B64D 2013/0651; B01D 46/0028; B01D 46/0036; B01D 46/2411; B01D 46/521
See application file for complete search history.

(56) References Cited

U.S. PATENT DOCUMENTS

| | | |
|---|---|---|
| 6,783,578 B2 | 8/2004 | Tillman, Jr. |
| 2004/0112221 A1 | 6/2004 | Tillman |
| 2015/0338336 A1* | 11/2015 | Dobrinsky ................ A61L 9/20 |
| | | 250/435 |
| 2016/0317694 A1* | 11/2016 | Leonaggeo ........ B01D 53/0407 |
| 2018/0250430 A1 | 9/2018 | Machovina et al. |
| 2019/0009912 A1 | 1/2019 | Matsui |
| 2021/0393841 A1 | 12/2021 | Vandyke |
| 2023/0045428 A1* | 2/2023 | Guillard .................... A61L 2/10 |

FOREIGN PATENT DOCUMENTS

| | | |
|---|---|---|
| JP | 2017074943 A | 4/2017 |
| KR | 20120047175 A | 5/2012 |
| WO | 2017101618 A1 | 6/2017 |
| WO | 2019195217 A1 | 10/2019 |

OTHER PUBLICATIONS

European Search Report and Written Opinion issued in European Patent Application No. 21170882.1, Mailing Date Oct. 4, 2021, 11 pages.

* cited by examiner

APPARATUS AND METHOD FOR IRRADIATING AIR IN AN AIR CIRCULATION SYSTEM OF A VEHICLE

CROSS-REFERENCE TO RELATED APPLICATIONS

The present application claims the priority to U.S. Provisional Patent Application No. 63/041,717, filed Jun. 19, 2020, the entire contents of which are incorporated by reference herein.

FIELD

The present disclosure relates to irradiation treatment of air within an air circulation system of a vehicle, and more particularly to air purification for use with cooling and environmental control systems onboard an aircraft.

BACKGROUND

This section provides background information related to the present disclosure which is not necessarily prior art. Cabin air systems in example vehicles and aircraft are designed to provide a comfortable cabin environment. In some example aircraft, the aircraft cabin is pressurized to enable passengers and crew to breathe normally. Air enters a passenger area from overhead distribution outlets that run a length of the aircraft cabin and generate airflow within the cabin. Air supplied to the cabin contains a mixture of recirculated air from within the cabin and air from outside the aircraft. Air is exhausted through air returns located along the length of the cabin, such that air is supplied to and exhausted from the passenger area on a continuous basis.

Other vehicles, such as trains and buses, have air circulation systems that circulate air for purposes of passenger comfort. In many vehicles, there is a centralized air unit that may circulate both external air introduced into the vehicle as well as air re-circulated inside the vehicle, where contaminants and airborne particulates may be present in the air. Airborne particulates include a complex mixture of organic and inorganic substances, including bacteria, germs, a variety of airborne viruses, and other substances that are small enough to become suspended in the air, where exposure of passengers to airborne particulates poses risks of infection and contagion.

Those skilled in the art will readily appreciate that all of the above-mentioned issues may represent significant considerations with respect to the overall operations of an airline or other vehicle operator. Thus, there exists a continuing need for an improved, cost-effective approach for circulating air within a vehicle.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

SUMMARY

This section provides a general summary of the disclosure, and is not a comprehensive disclosure of its full scope or all of its features.

According to various aspects, an apparatus for irradiating air within an air circulation system of a vehicle includes a filter unit to couple to a recirculating air conduit that is coupled to an air circulation system. A filter is disposed in an inlet end of the filter unit, and includes an outer High Efficiency Particulate Air (HEPA) media filter, and an inner activated carbon filter media defining an interior volume. The apparatus further includes a plurality of ultraviolet light transmissive strands that each have distal ends disposed in a spaced apart manner in an interface between the outer HEPA media filter and the inner activated carbon filter, and proximal ends connectable to an ultraviolet light emitting source such that ultraviolet light is transmitted by the transmissive strands into an interface region between the outer HEPA media filter and the inner activated carbon filter. The ultraviolet light transmissive strands can receive emitted ultraviolet light that is substantially between 222 nm and 265 nm for irradiating air passing through the filter.

According to another aspect, a method for irradiating air in an air circulation system of a vehicle includes coupling a filter unit to a recirculating air conduit that is connected to an air circulation system. The method includes positioning the distal ends of a plurality of ultraviolet light transmissive strands in a spaced apart manner along an outer surface of an activated carbon filter, and positioning the activated carbon filter within a High Efficiency Particulate Air (HEPA) media filter, such that the distal ends of a plurality of ultraviolet light transmissive strands are disposed along an interface region between the outer HEPA media filter and the inner activated carbon filter. The method further includes securing the filter including the ultraviolet light transmissive strands relative to the filter unit, and connecting a proximal end of each of the plurality of ultraviolet light transmissive strands to an ultraviolet light emitting source such that ultraviolet light emitted by the source is transmitted by the transmissive strands into an interface region between the outer HEPA media filter and the inner activated carbon filter. The method further includes activating the ultraviolet light emitting source, to cause the ultraviolet light source to emit ultraviolet radiation substantially at between 222 nm and 253 nm that is transmitted by the transmissive strands for irradiating air passing through the filter into the air circulation system.

Further areas of applicability will become apparent from the description herein. The description and specific examples in the summary are intended for purposes of illustration only and are not intended to limit the scope of the present disclosure.

Various refinements exist of the features noted above in relation to the various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. Again, the brief summary presented above is intended only to familiarize the reader with certain aspects and contexts of the present disclosure without limitation to the claimed subject matter.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings. According to various aspects of the present disclosure, embodiments are described of an apparatus for irradiation treatment of air within an air circulation system of a vehicle. The features, functions, and advantages discussed in the preceding section can be achieved independently in various embodiments or may be combined in yet other embodiments. Further aspects of the present disclosure can be seen with reference to the drawings and following described embodiments.

In an example, an apparatus for irradiation treatment of air within an air circulation system of a vehicle includes a filter unit configured to couple to a recirculating-air conduit coupled to an air circulation system, the filter unit having an inlet end. A filter is disposed in the inlet end of the filter unit, and includes an outer High Efficiency Particulate Air (HEPA) media filter, and an inner activated carbon filter media defining an interior volume. The apparatus further includes a plurality of ultraviolet light transmissive strands that each have distal ends disposed in a spaced apart manner in an interface between the outer HEPA media filter and the inner activated carbon filter, and proximal ends connectable to an ultraviolet light emitting source such that ultraviolet light is transmitted by the transmissive strands into an interface region between the outer HEPA media filter and the inner activated carbon filter. The ultraviolet light transmissive strands are configured to receive emitted ultraviolet light that is substantially between 222 nm and 265 nm for irradiating air passing through the filter.

Figure 1:
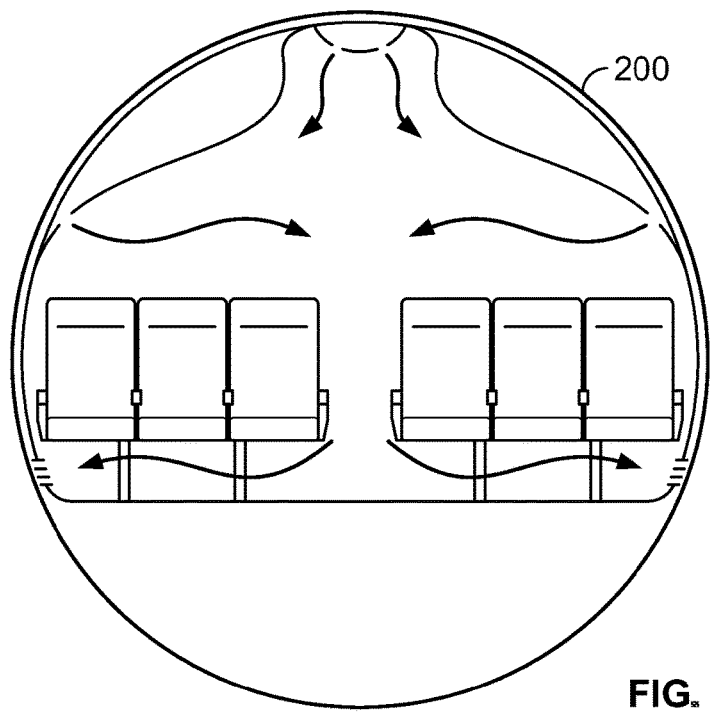
FIG. 1 is an illustration of a vehicle including an aircraft, the vehicle having a passenger air distribution system that receives air from an air circulation system, according to the present disclosure.

Referring to FIG. 1, a vehicle including an aircraft 200 has a passenger air distribution system that receives air from an air circulation system. The air distribution system supplies air that enters a passenger area from overhead distribution outlets that run a length of the aircraft cabin and generate airflow in the cabin. Air supplied to the cabin contains a mixture of recirculated air from in the cabin and air from outside the aircraft. Air is drawn through air returns located near the floor along the length of the cabin, such that air is supplied to and removed from the cabin passenger area on a continuous basis.

Figure 2:
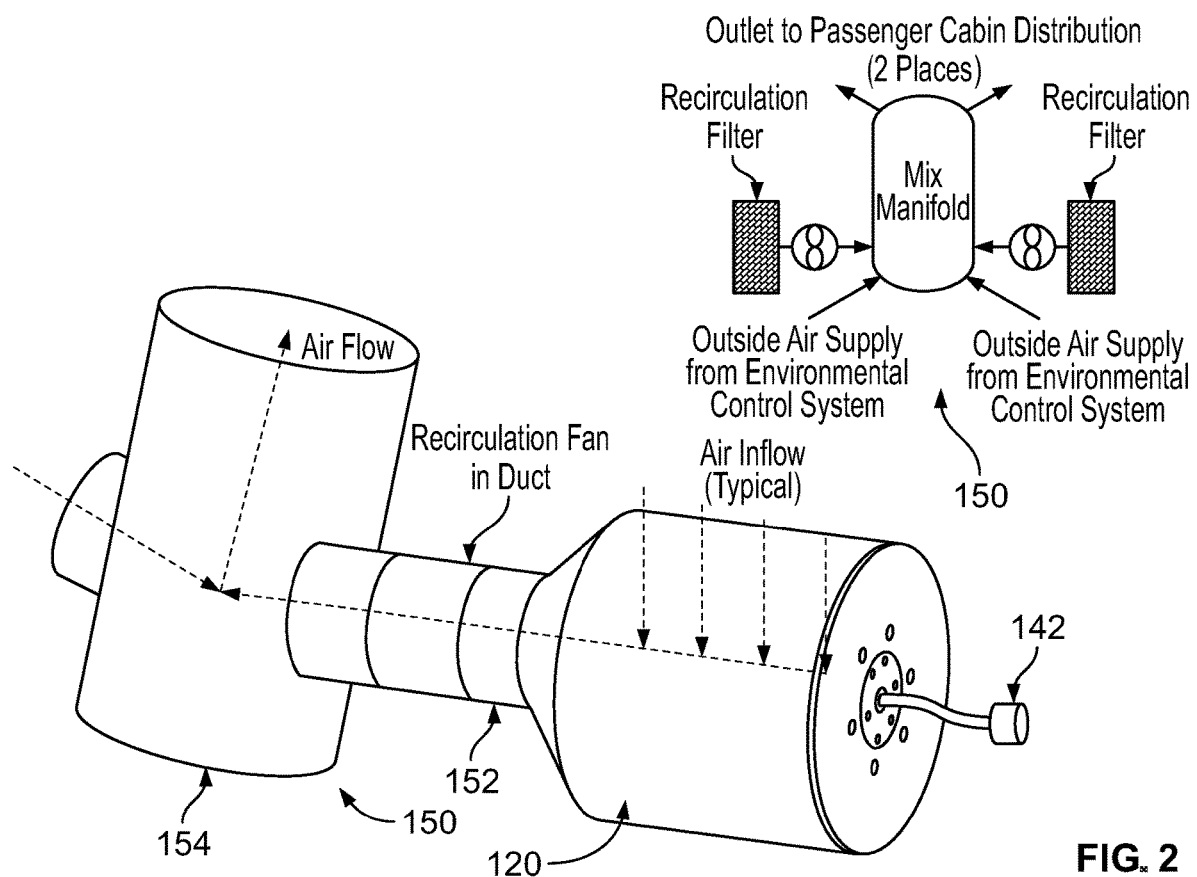
FIG. 2 is an illustration of an air circulatory system of a vehicle including an embodiment of an apparatus for irradiating air flow to the air circulation system, according to the present disclosure.

FIG. 2 is an illustration of an air circulation system 150 of a vehicle—such as the aircraft 200 shown in FIG. 1—including an embodiment of an apparatus for irradiating air flow to the air circulation system 150. The air circulation system 150 includes a recirculating-air conduit 152 (in which a recirculating fan may be disposed) that is connected to a mix manifold 154 of the air circulation system 150, where the mix manifold 154 receives supply of outside air from outside the aircraft 200 from an Environmental Control System (ECS) and also receives recirculated air via filtered inputs. The mix manifold 154 also supplies two air distribution lines to supply circulated air to passengers in the cabin.

Figure 3:
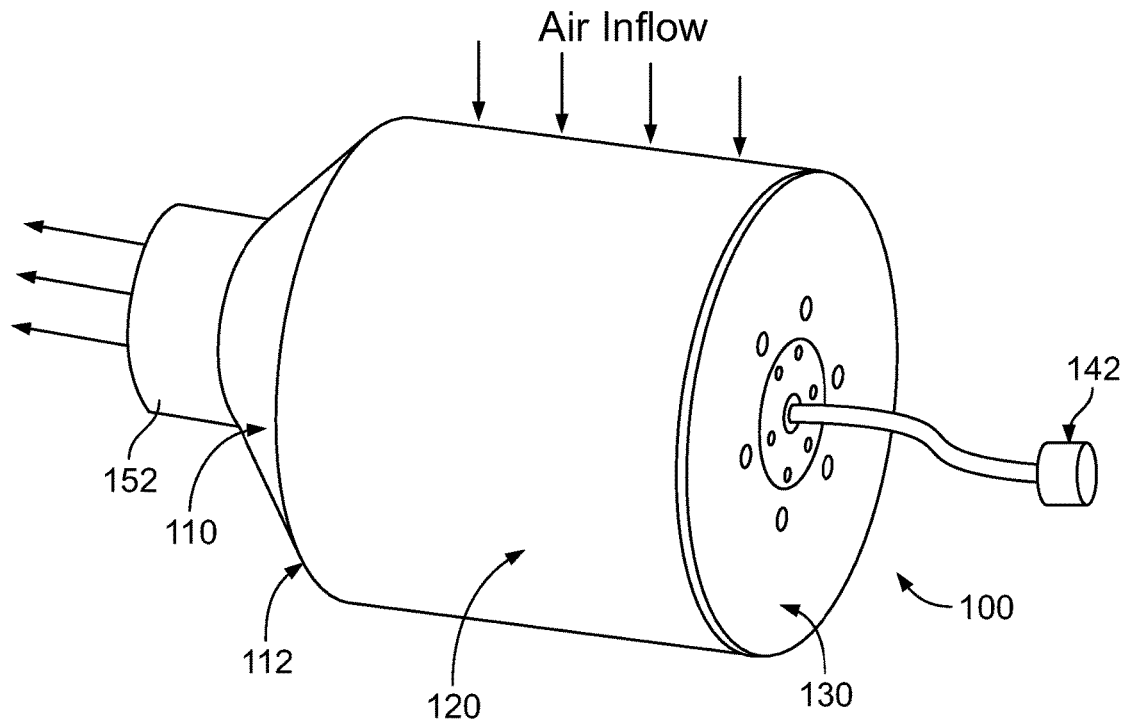
FIG. 3 is an illustration of an embodiment of an apparatus for irradiating air flow in the air circulation system for a vehicle, such as that shown in FIGS. 1 and 2, according to the present disclosure.

FIG. 3, depicts an embodiment of an apparatus 100 for irradiation treatment of air within an air circulation system 150 such as that shown in FIG. 2, for a vehicle such as aircraft 200 in FIG. 1. The apparatus 100 includes a filter unit 110 configured to couple to a recirculating air conduit 152 connected to the mix manifold 154 of the air circulation system 150, where the filter unit 110 has an inlet end 112. A filter 120 is disposed in the inlet end 112 of the filter unit 110, and includes an outer High Efficiency Particulate Air (HEPA) media filter 120A and an inner activated carbon filter 120B (not shown in FIG. 3). The apparatus 100 further includes a plurality of ultraviolet light transmissive strands that each have distal ends disposed in a spaced apart manner in an interface between the outer HEPA media filter 120A and the inner activated carbon filter 120B, and proximal ends connectable to an ultraviolet light emitting source such that ultraviolet light is transmitted by the transmissive strands into an interface region between the outer HEPA media filter 120A and the inner activated carbon filter 120B. The apparatus 100 further comprises an end plate 130, configured to be mounted with the end plate 130 against an open end of the filter 120, wherein the ultraviolet light transmissive strands are configured to transmit ultraviolet radiation substantially at between 222 nm and 253 nm for irradiating air passing through the filter 120 into the air circulation system 150.

In an embodiment, the apparatus 100 includes the filter unit 110 that is coupled to the recirculating air conduit 152, which is connected to the mix manifold 154 of the air circulation system 150. The filter 120 is disposed at the inlet end 112 of the filter unit 110, where the filter 120 may have a circular, rectangular, or triangular shape and an outer surface through which air is drawn, where the filter shape defines an interior volume through which air passes through the media of the filter 120 to the interior volume. The outer High Efficiency Particulate Air (HEPA) filter 120A may include an outer annular portion of the filter 120 forming a pleated cartridge made with a High Efficiency Particulate Air (HEPA) media, and the inner activated carbon filter 120B may include an inner annular portion of the filter 120 that includes activated carbon. The filter 120 may have a cylindrical shape, and may include the outer High Efficiency Particulate Air (HEPA) media 120A and the inner activated carbon filter media 120B defining an interior volume of the filter 120. More specifically, in some embodiment, the outer pleated High Efficiency Particulate Air (HEPA) media 120A includes an outer annular portion of the filter 120 forming a pleated cartridge made with a High Efficiency Particulate Air (HEPA) media, and the inner activated carbon filter media 120B includes an inner annular portion of the filter 120 that includes activated carbon.

Figure 4:
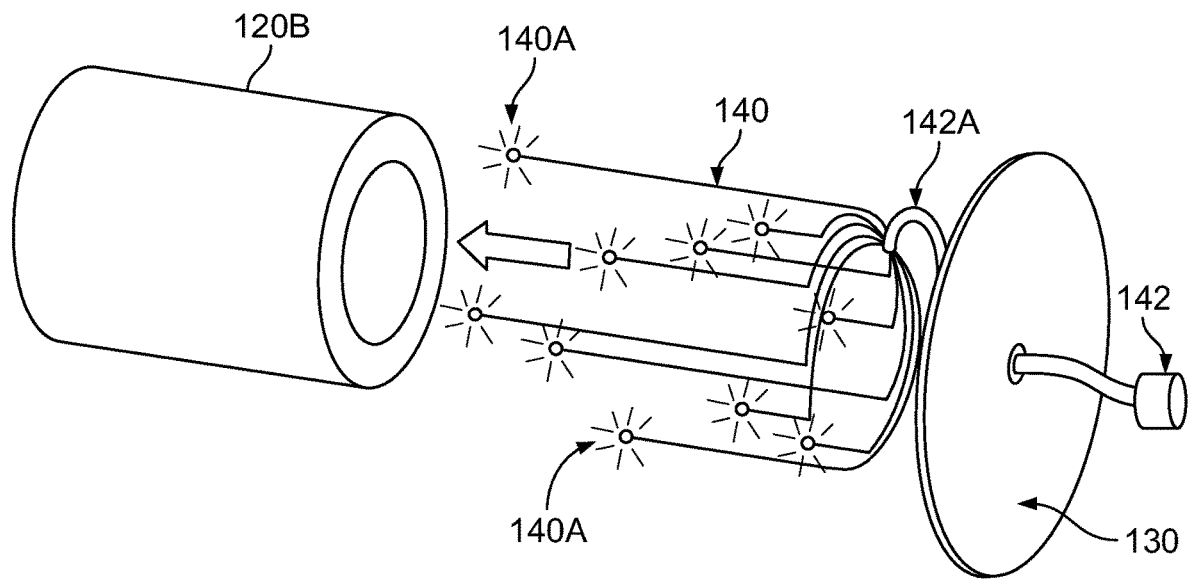
FIG. 4 is an illustration of the apparatus in FIG. 3 depicting the ultraviolet light transmissive strands for a filter, according to the present disclosure.
Figure 5:
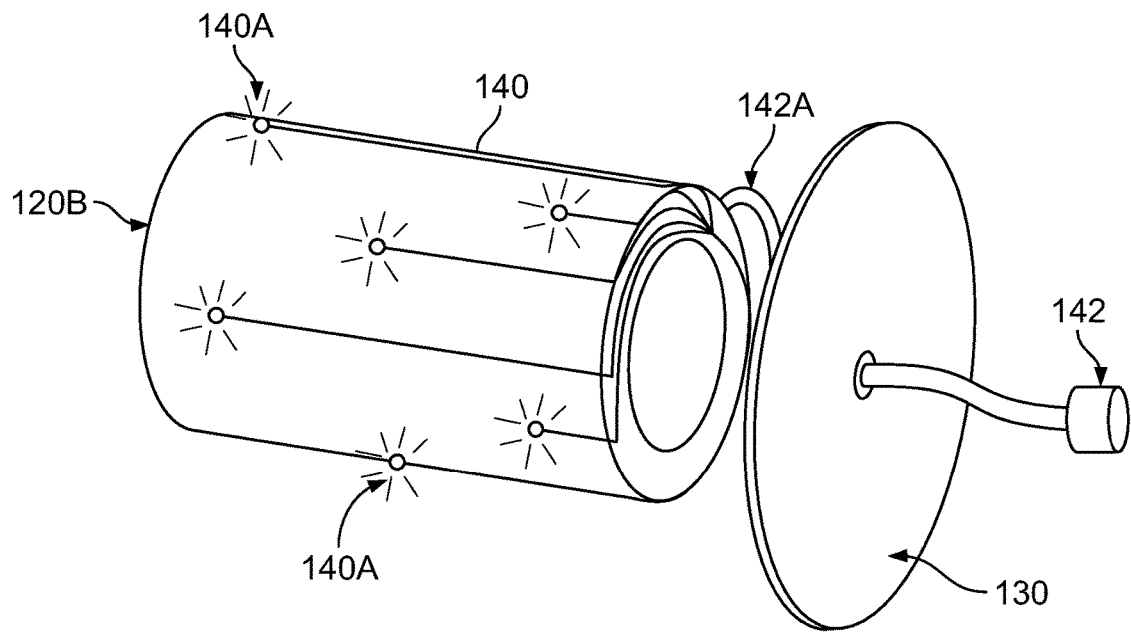
FIG. 5 is an illustration of the apparatus in FIG. 4 with the ultraviolet light transmissive strands on part of the filter, according to the present disclosure.
Figure 6:
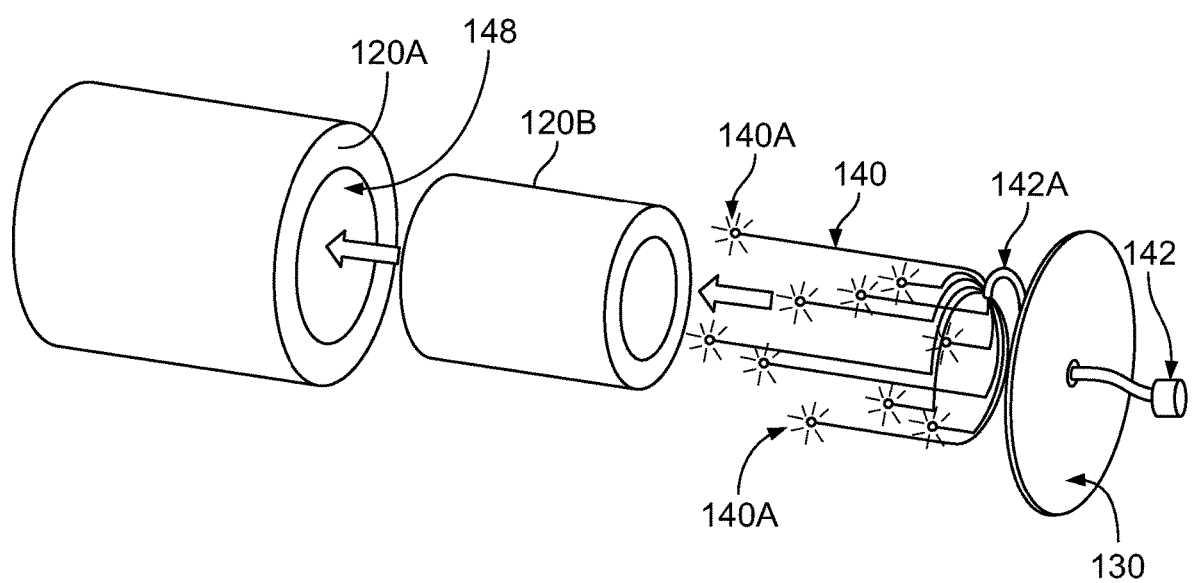
FIG. 6 is an assembly view of the apparatus in FIG. 5 depicting the ultraviolet light transmissive strands relative to an open end of the filter in the apparatus in FIG. 3, according to the present disclosure.

In an exemplary embodiment shown in FIG. 4, the apparatus 100 includes a plurality of ultraviolet light transmissive strands 140 that each have distal ends 140A disposed in a spaced apart manner in an interface region 148 (see FIG. 6) between the outer HEPA media filter 120A and the inner activated carbon filter 120B, and proximal ends connectable to an ultraviolet light emitting source such that ultraviolet light is transmitted by the transmissive strands into the interface region 148 between the outer HEPA media filter 120A and the inner activated carbon filter 120B. The ultraviolet light transmissive strands 140 may be overlaid on or disposed on an outer surface of the inner activated carbon filter 120B, such that the distal ends 140A of the plurality of ultraviolet light transmissive strands 140 are positioned in a spaced apart manner along an outer surface of the activated carbon filter 120B, as shown in FIG. 5. The transmissive strands 140 overlaid on the activated carbon filter 120B are then positioned within the outer High Efficiency Particulate Air (HEPA) media filter 120A, as shown in FIG. 6, such that the distal ends 140A of the plurality of ultraviolet light transmissive strands 140 are disposed along the interface region 148 between the outer HEPA media filter 120A and the inner activated carbon filter 120B. In some embodiments, the distal ends 140A of the plurality of ultraviolet light transmissive strands 140 are removably disposed between the outer HEPA media filter 120A and the inner activated carbon filter 120B, such that they can be removed and replaced. The proximal end of each of the plurality of ultraviolet light transmissive strands 140 are connected to an ultraviolet light emitting source, such that ultraviolet light emitted by the source is transmitted by the transmissive strands 140 into the interface region 148 between the outer HEPA media filter 120A and the inner activated carbon filter 120B. The filter 120 including the ultraviolet light transmissive strands 140 is positioned relative to the filter unit 110, and the end plate 130 is positioned against the open end of the filter 120.

The distal ends 140A of the plurality of ultraviolet light transmissive strands 140 may each be of varying lengths, such that the distal ends 140A are positioned at different locations within the interface region 148 between the outer HEPA media filter 120A and the inner activated carbon filter 120B. The distal ends 140A of the plurality of ultraviolet light transmissive strands 140 may be positioned at various locations within the interface region 148 between the outer HEPA media filter 120A and the inner activated carbon filter 120B, such that ultraviolet light is scattered throughout the interface region 148. In some embodiments, the outer HEPA media filter 120A is made of woven fiberglass, where the transmitted ultraviolet light emitted at the interface region 148 is reflected and scattered by the woven fiberglass to disperse UV light and irradiate the interface region 148 between the outer HEPA media filter 120A and the inner activated carbon filter 120B. In some embodiments, the proximal ends of the plurality of ultraviolet light transmissive strands 140 are joined into a single strand that is positioned relative to an ultraviolet light source, and may be connected to a connector proximate to the end plate 130. In some embodiments, the ultraviolet light source emits ultraviolet radiation at between 222 nm and 265 nm at a power flux or irradiation of at least 1,000 microwatts per square centimeter, such that the intensity of ultraviolet radiation is sufficient to kill and/or degrade microorganisms, viruses, bacteria, germs, mold, and other contaminants in the air flowing through the filter. In some embodiments, the plurality of ultraviolet light transmissive strands 140 include optical fibers suitable for fiber-optic transmission of ultraviolet light. One such optical fiber is Molex® Silica Optical Fiber sold by Laser Components. In some embodiments, the apparatus 100 further includes, as an ultraviolet light source, an ultraviolet light emitting diode (LED) positioned relative to the proximal ends of the plurality of ultraviolet light transmissive strands 140 including optical fibers, where the ultraviolet LED emits ultraviolet light into the proximal ends of the ultraviolet light transmissive strands 140, which transmit the ultraviolet light to the interface region 148 to irradiate the air passing through the outer HEPA media filter 120A, the interface region 148, and the inner activated carbon filter 120B into the air circulation system 150. One example may be an ultraviolet LED part number VPS134 sold by Boston Scientific. In some embodiments, the ultraviolet light source is configured to emit a distribution of frequencies of ultraviolet radiation ranging substantially at between 222 nm and 265 nm, where the range is sufficient to result in generation of a minimal amount of ozone. An ultraviolet light source having a wavelength below 240 nm can generate ozone, while an ultraviolet light source having an emission frequency in the range of about 240 nm to 265 nm can potentially destroy ozone or reduce the level of ozone, where the emission of a range of ultraviolet radiation up to a frequency of 265 nm potentially reduces or limits the extent of ozone generated by emitted UV radiation at lower frequencies, such that the distribution of frequencies in the range of between 222 nm and 265 nm results in generation of a minimal amount of ozone within the filter 120. The filter 120 including the ultraviolet light transmissive strands 140 is positioned relative to the filter unit 110, and an end plate 130 is positioned against the open end of the filter 120. The end plate 130 shown in FIG. 6 is, in some embodiments, configured to be mounted by attachment via rivets, adhesive, or bonding to the end of the filter 120.

Figure 7:
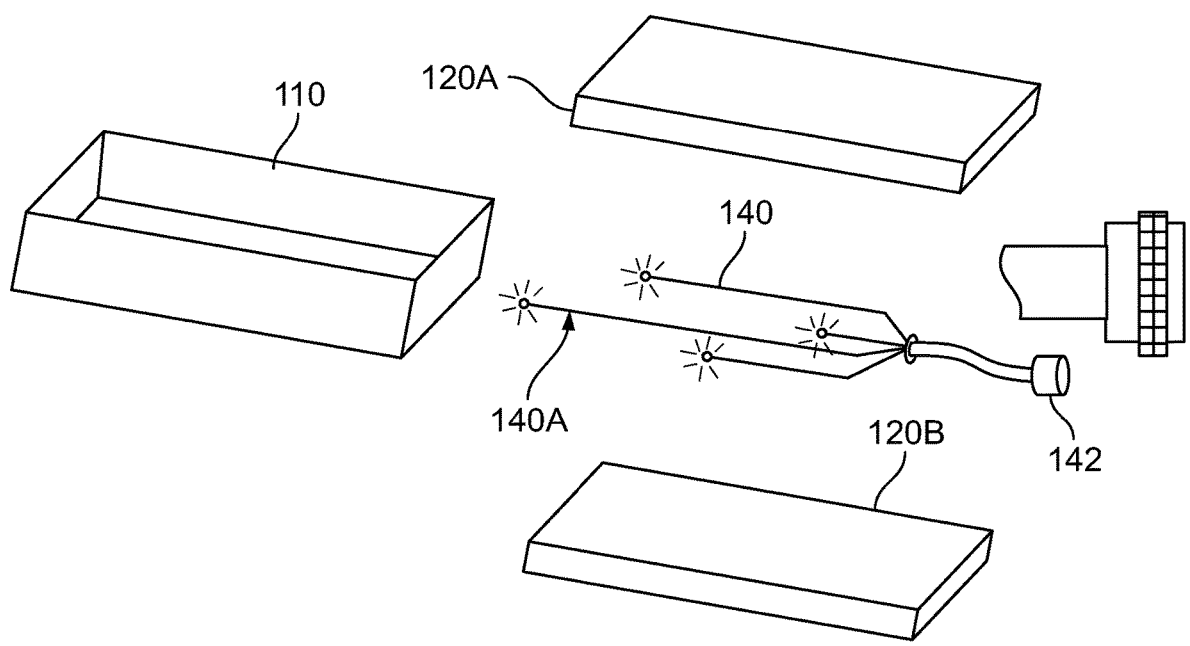
FIG. 7 is an assembly view of another embodiment of a filter including ultraviolet light transmissive strands, according to the present disclosure.
Figure 8:
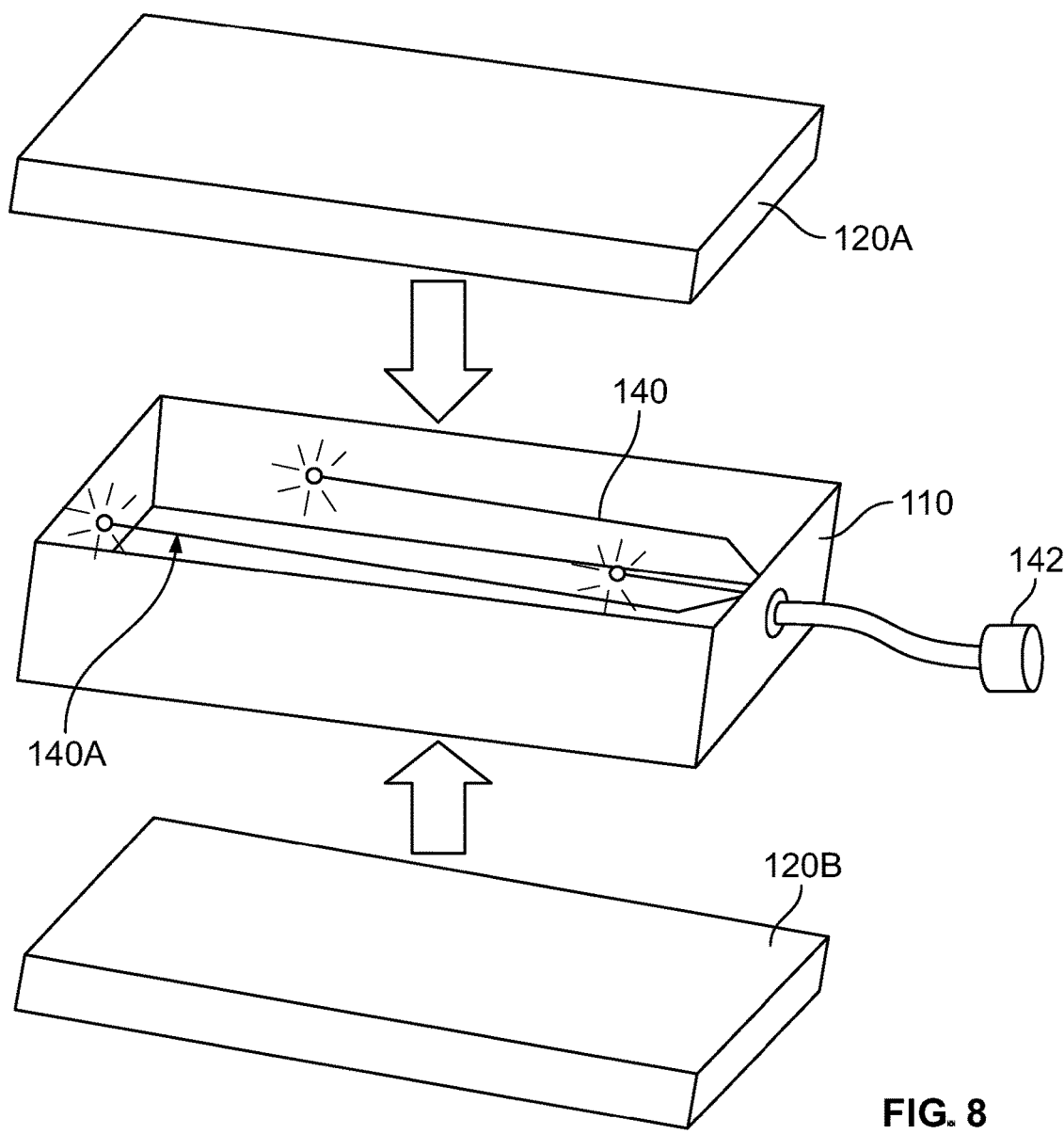
FIG. 8 is an illustration of the embodiment in FIG. 7 depicting the ultraviolet light transmissive strands disposed at an interface between a HEPA filter and an activated carbon filter, according to the present disclosure.
Figure 9:
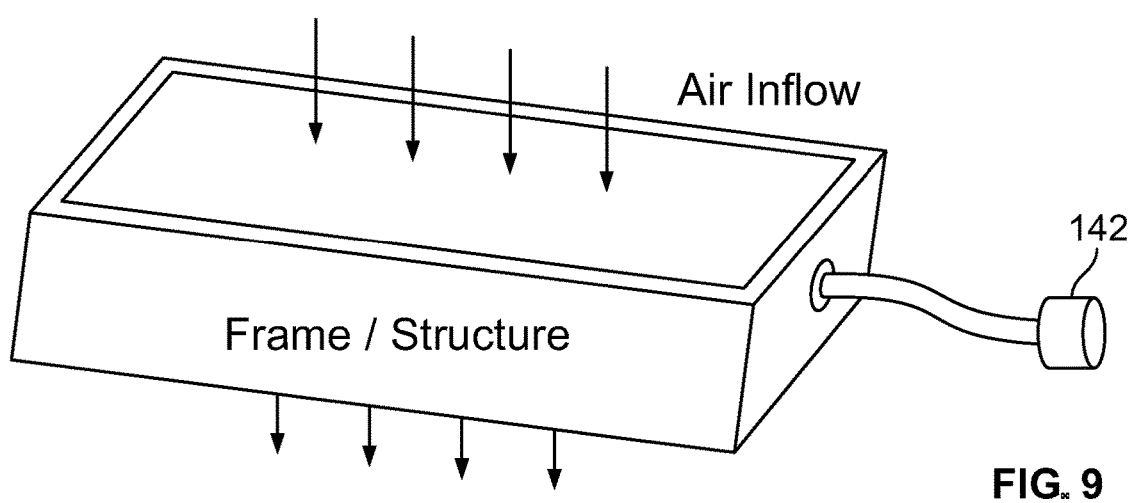
FIG. 9 is an assembly view of another embodiment of a filter including ultraviolet light transmissive strands, according to the present disclosure.

Referring to FIG. 7, another embodiment is shown of a filter (e.g., the filter 120) including ultraviolet light transmissive strands 140, which may be included in the apparatus 100 for irradiating air in an air circulation system (e.g., the air circulation system 150). The filter includes a filter unit 110 (or filter housing), a plurality of ultraviolet light transmissive strands 140, a HEPA filter 120A, and an activated carbon filter 120B. As shown in FIG. 8, the distal ends 140A of the plurality of ultraviolet light transmissive strands 140 are positioned within an interface region 148 between the HEPA filter 120A and an activated carbon filter 120B such that the plurality of ultraviolet light transmissive strands 140 are disposed between the HEPA filter 120A and the activated carbon filter 120B. The proximal ends of the plurality of ultraviolet light transmissive strands 140 pass through a sealed connection in the filter unit 110, where an ultraviolet light source may be positioned relative to (or connected to) the plurality of ultraviolet light transmissive strands 140 such that ultraviolet light emitted by the source is transmitted by the plurality of ultraviolet light transmissive strands 140.

Additionally, the apparatus 100 may be configured to include a controller (not shown) that monitors an air flow sensor, mass flow sensor, or air particulate sensor disposed within the cabin of the aircraft (e.g., aircraft 200, shown in FIG. 1), to determine if the amount of recirculated irradiated air flow through the aircraft cabin is indicative of a minimum level for removing airborne particulates and contaminates, and thereafter discontinuing supply of power to the ultraviolet light source positioned relative to (or connected to) the plurality of ultraviolet light transmissive strands 140. Similarly, the controller can monitor the sensor to determine if a measurement is indicative of the presence of more than an acceptable threshold of ozone or contaminant particulates are present in the cabin air, and thereafter deactivating the ultraviolet light emitter to discontinue ultraviolet light irradiation. Additionally, the controller may monitor the sensor to determine if the amount of recirculated irradiated air flow through the aircraft cabin is indicative of an insufficient level for removing airborne particulates and contaminates, and thereafter initiate the supply of power to the ultraviolet light to emit ultraviolet radiation at between 222 nm and 265 nm to irradiate the air flow through the filter 120 into the air circulation system 150.

According to another aspect, a method for irradiating air within an air circulation system of a vehicle includes coupling a filter unit to a recirculating-air conduit that is connected to a manifold of an air circulation system, the filter unit having an inlet end. The method further includes positioning the distal ends of a plurality of ultraviolet light transmissive strands in a spaced apart manner along an outer surface of an activated carbon filter, and positioning the activated carbon filter within a High Efficiency Particulate Air (HEPA) media filter, such that the distal ends of a plurality of ultraviolet light transmissive strands are disposed along an interface region between the outer HEPA media filter and the inner activated carbon filter. The method further includes securing the filter including the ultraviolet light transmissive strands relative to the filter unit, and connecting a proximal end of each of the plurality of ultraviolet light transmissive strands to an ultraviolet light emitting source such that ultraviolet light emitted by the source is transmitted by the transmissive strands into an interface region between the outer HEPA media filter and the inner activated carbon filter. The method further includes activating the ultraviolet light emitting source, to cause the ultraviolet light source to emit ultraviolet radiation substantially at between 222 nm and 265 nm that is transmitted by the transmissive strands for irradiating air passing through the filter into the air circulation system.

Figure 10:
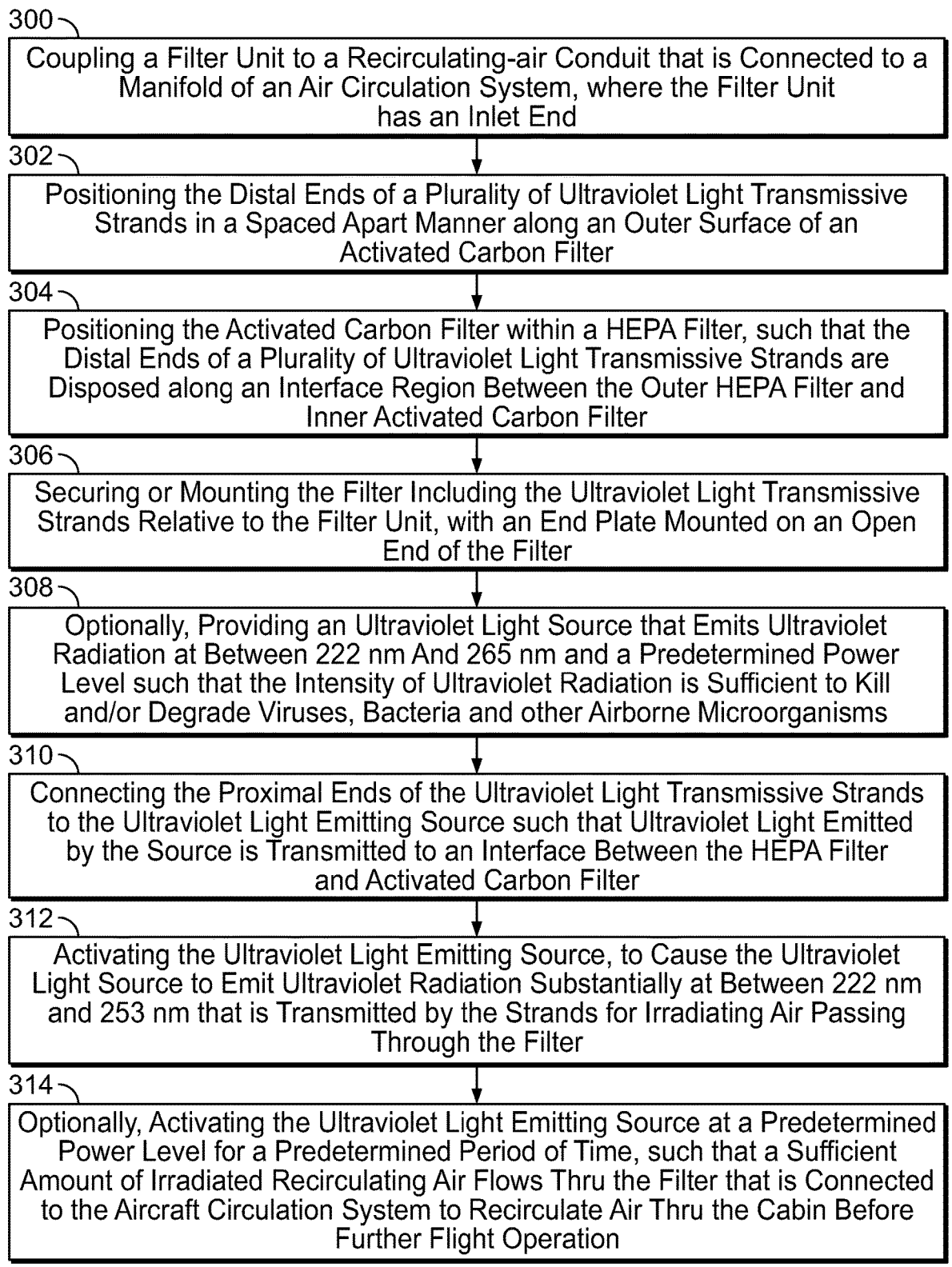
FIG. 10 is an illustration of a method for irradiating air within an air circulation system of a vehicle in accordance with the present disclosure.

As illustrated in FIG. 10, one embodiment of a method is provided for irradiating air within an air circulation system of a vehicle. The method includes at step 300 coupling a filter unit to a recirculating-air conduit that is connected to a manifold of an air circulation system, the filter unit having an inlet end. The method includes, at step 302, positioning the distal ends of a plurality of ultraviolet light transmissive strands in a spaced apart manner along an outer surface of an activated carbon filter. The method further includes, at step 304, positioning the activated carbon filter within a High Efficiency Particulate Air (HEPA) media filter, such that the distal ends of a plurality of ultraviolet light transmissive strands are disposed along an interface region between the outer HEPA media filter and the inner activated carbon filter. At step 306, the method includes securing the filter including the ultraviolet light transmissive strands relative to the filter unit, and an end plate positioned against an open end of the filter. The method may optionally include the step 308 of providing an ultraviolet light source that emits ultraviolet radiation at between 222 nm and 265 nm and a predetermined power level such that an intensity of the ultraviolet radiation is sufficient to kill and/or degrade viruses, bacteria, and other airborne microorganisms. The method further includes, at step 310, connecting a proximal end of each of the plurality of ultraviolet light transmissive strands to an ultraviolet light emitting source such that activation of the source causes ultraviolet light emitted by the source to be transmitted by the transmissive strands into an interface region between the outer HEPA media filter and the inner activated carbon filter, for irradiating air flow passing through the filter into an air circulation system. The method further includes, at step 312, activating the ultraviolet light emitting source, to cause the ultraviolet light source to emit ultraviolet radiation substantially at between 222 nm and 265 nm that is transmitted by the transmissive strands for irradiating air passing through the filter into the air circulation system. The method may optionally include the step 314 of activating the ultraviolet light source to emit ultraviolet radiation at a predetermined power level for a predetermined period of time, such that a sufficient amount of irradiate recirculating air flows through the air circulation system and aircraft cabin before further flight operation of the aircraft.

The example embodiments fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

The foregoing description of the embodiments has been provided for purposes of illustration and description. It is not intended to be exhaustive or to limit the present disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. An apparatus for irradiating air in an air circulation system of a vehicle, the apparatus comprising:
   a filter unit configured to couple to a recirculating air conduit connected to the air circulation system, the filter unit having an inlet end;
   a filter disposed in the inlet end of the filter unit, comprising an outer High Efficiency Particulate Air (HEPA) media filter, and an inner activated carbon filter defining an interior volume of the filter;
   a plurality of ultraviolet light transmissive strands that each have distal ends disposed in a spaced apart manner in an interface between the outer HEPA media filter and the inner activated carbon filter, and proximal ends connectable to an ultraviolet light emitting source such that ultraviolet light is transmitted by the plurality of ultraviolet light transmissive strands into an interface region between the outer HEPA media filter and the inner activated carbon filter; and
   an end plate disposed over an open end of the filter, having an aperture though which the plurality of ultraviolet light transmissive strands extend,
   wherein the ultraviolet light transmissive strands are configured to receive emitted ultraviolet light that is substantially at between 222 nm and 265 nm, and to transmit the ultraviolet light into the air passing through the interface between the outer HEPA media filter and the inner activated carbon filter and into the air circulation system, and
   wherein each of the distal ends of the plurality of ultraviolet light transmissive strands are of varying lengths, such that the distal ends are positioned at different locations within the interface between the outer HEPA media filter and the inner activated carbon filter.

2. The apparatus of claim 1, wherein the ultraviolet light is configured to emit a distribution of frequencies of ultraviolet radiation ranging substantially between 222 nm and 265 nm.

3. The apparatus of claim 1, wherein the proximal ends of the plurality of ultraviolet light transmissive strands are joined into a single strand that is connected to a connector proximate to the end plate.

4. The apparatus of claim 3, wherein the ultraviolet light emitting source emits ultraviolet radiation at between 222 nm and 265 nm at a power flux or irradiation of at least 1,000 microwatts per square centimeter, such that an intensity of the ultraviolet radiation is sufficient to kill and/or degrade microorganisms, viruses, bacteria, germs, mold, and other contaminants in the air flowing through the interior volume of the filter.

5. The apparatus of claim 1, wherein the plurality of ultraviolet light transmissive strands comprises optical fibers suitable for fiber-optic transmission of ultraviolet light.

6. The apparatus of claim 5, further comprising an ultraviolet light emitting diode (LED) positioned relative to the proximal ends of the plurality of ultraviolet light transmissive strands comprising optical fibers, where the ultraviolet light emitting diode emits ultraviolet light into the proximal ends of the optical fibers that transmit the ultraviolet light to irradiate the air passing through the outer HEPA media filter, the interface region and the inner activated carbon filter into the air circulation system.

7. The apparatus of claim 1, wherein the end plate is configured to be mounted by attachment via rivets, adhesive, or bonding to an open end of the filter.

8. The apparatus of claim 1, wherein the outer HEPA media comprises an outer annular portion of the filter forming a pleated cartridge made with a HEPA media.

9. The apparatus of claim 8, wherein the inner activated carbon filter comprises an inner annular portion of the filter that includes activated carbon.

10. The apparatus of claim 9, wherein the recirculating air conduit is connected to a manifold of the air circulation system of the vehicle, and wherein the filter unit filters recirculating air supplied to the manifold.

11. The apparatus of claim 10, wherein the manifold is a mixing manifold of the air circulation system on board an aircraft.

12. A method for irradiating air in an air circulation system of a vehicle, comprising the steps of:
   coupling a filter unit to a recirculating-air conduit that is connected to a manifold of the air circulation system, the filter unit having an inlet end;
   positioning distal ends of a plurality of ultraviolet light transmissive strands in a spaced apart manner along an outer surface of an inner activated carbon filter of a filter, wherein each of the distal ends of the plurality of ultraviolet light transmissive strands are of varying lengths and positioned at different locations; positioning the inner activated carbon filter within an outer High Efficiency Particulate Air (HEPA) media filter of the filter, such that the distal ends of the plurality of ultraviolet light transmissive strands are disposed along an interface region between the outer HEPA media filter and the inner activated carbon filter;
   securing the filter including the ultraviolet light transmissive strands relative to the filter unit, and an end plate positioned against an open end of the filter;
   connecting a proximal end of each of the plurality of ultraviolet light transmissive strands to an ultraviolet light emitting source such that ultraviolet light emitted by the source is transmitted by the plurality of ultraviolet light transmissive strands into the interface region between the outer HEPA media filter and the inner activated carbon filter; and
   activating the ultraviolet light emitting source, to cause the ultraviolet light emitting source to emit ultraviolet radiation substantially at between 222 nm and 265 nm that is transmitted by the plurality of ultraviolet light transmissive strands for irradiating air passing through the filter into the air circulation system.

13. The method of claim 12, wherein the method further comprises positioning the proximal ends of the plurality of ultraviolet light transmissive strands, comprising joining the plurality of ultraviolet light transmissive strands into a single bundled strand such that the ultraviolet light emitting source emits ultraviolet light into the plurality of ultraviolet light transmissive strands.

14. The method of claim 13, wherein the step of activating the ultraviolet light emitting source comprises operating an ultraviolet light emitting diode that emits ultraviolet radiation at between 222 nm and 265 nm, at a power flux or irradiation of at least 1,000 microwatts per square centimeter, such that an intensity of the ultraviolet radiation irradiating the air passing through the filter is sufficient to kill and/or degrade microorganisms, viruses, bacteria, germs, mold and other contaminants in the air flowing through the filter.

15. The method of claim 13, wherein the method further comprises coupling a housing of the filter unit to the recirculating air conduit that is connected to the manifold of the air circulation system of an aircraft, for enabling supply of irradiated recirculating air to the manifold of the air circulation system for the aircraft.

16. The method of claim 14, further comprising the step of powering the ultraviolet light emitting source to power the ultraviolet light for a predetermined period of time, such that a sufficient amount of irradiated recirculating air flows through the manifold and is recirculated through a cabin of the vehicle before further operation of the vehicle.

17. The method of claim 16, further comprising the step of monitoring a sensor disposed within the cabin of the vehicle to determine if the amount of recirculated irradiated air flow through the cabin of the vehicle is indicative of a minimum level for removing airborne particulates and contaminates, and thereafter discontinuing supply of power to the ultraviolet light emitting source.

18. The method of claim 17, further comprising monitoring the sensor disposed within the cabin of the vehicle to determine if a measurement of recirculated irradiated air flow through the cabin of the vehicle is indicative of an insufficient level for removing airborne particulates and contaminates, and thereafter supplying power to the ultraviolet light emitting source to emit ultraviolet radiation at between 222 nm and 265 nm to irradiate the air flow through the filter into the air circulation system.

19. The method of claim 12, wherein the plurality of ultraviolet light transmissive strands comprises optical fibers suitable for fiber-optic transmission of ultraviolet light.

20. The method of claim 12, wherein the manifold is a mixing manifold of the air circulation system on board an aircraft.

* * * * *